United States Patent
Backman et al.

(10) Patent No.: US 7,534,599 B2
(45) Date of Patent: May 19, 2009

(54) SUPPORT FOR GROWTH MEDIUM

(75) Inventors: Henry Backman, Espoo (FI); Tapani Hellman, Espoo (FI); Antti Kaplas, Kerava (FI); Juhani Luotola, Espoo (FI); Jarmo Smolander, Helsinki (FI)

(73) Assignee: Orion Dianostica Oy, Espoo (FI)

( * ) Notice: Subject to any disclaimer, the term of this patent is extended or adjusted under 35 U.S.C. 154(b) by 705 days.

(21) Appl. No.: 10/486,791

(22) PCT Filed: Aug. 16, 2002

(86) PCT No.: PCT/FI02/00673

§ 371 (c)(1),
(2), (4) Date: Apr. 13, 2005

(87) PCT Pub. No.: WO03/016462

PCT Pub. Date: Feb. 27, 2003

(65) Prior Publication Data

US 2006/0121601 A1    Jun. 8, 2006

(30) Foreign Application Priority Data

Aug. 17, 2001  (FI) .................................. 20011660

(51) Int. Cl.
*C12M 3/00*   (2006.01)

(52) U.S. Cl. .............. 435/287.9; 435/288.1; 435/299.2; 435/304.1; 206/569; 422/61; 422/202; 422/914

(58) Field of Classification Search ................. 435/252, 435/288.1, 299.2, 304.1; 206/569; 422/913, 422/914, 915
See application file for complete search history.

(56) References Cited

U.S. PATENT DOCUMENTS

| 4,865,988 A | 9/1989 | Guala |
| 5,376,337 A * | 12/1994 | Seymour .................... 422/101 |

FOREIGN PATENT DOCUMENTS

| DE | 29 36 294 | 6/1980 |
| DE | 2 525 233 | 10/1983 |
| EP | 0 557 041 A1 | 8/1993 |
| FI | 46780 B | 2/1973 |
| GB | 2 141 136 A | 12/1984 |
| WO | WO-90/02169 | 3/1990 |

* cited by examiner

*Primary Examiner*—William H Beisner
*Assistant Examiner*—Michael Hobbs
(74) *Attorney, Agent, or Firm*—Connolly Bove Lodge & Hutz LLP

(57) ABSTRACT

The present invention is directed to a growth medium support plate including an essential planar body part extending therefrom. The growth medium support plate also includes a stem member for connecting a cap to the support plate. The stem member is connected to the body part so as to have a position co-planar with the body part and a position inclined to the plane of the body part. The support plate includes at least one fixed projection extending from and co-planar with said body part adjacently to the stem member and the stem member having in the position coplanar with the body part a releasable connection to the at least one fixed projection.

12 Claims, 4 Drawing Sheets

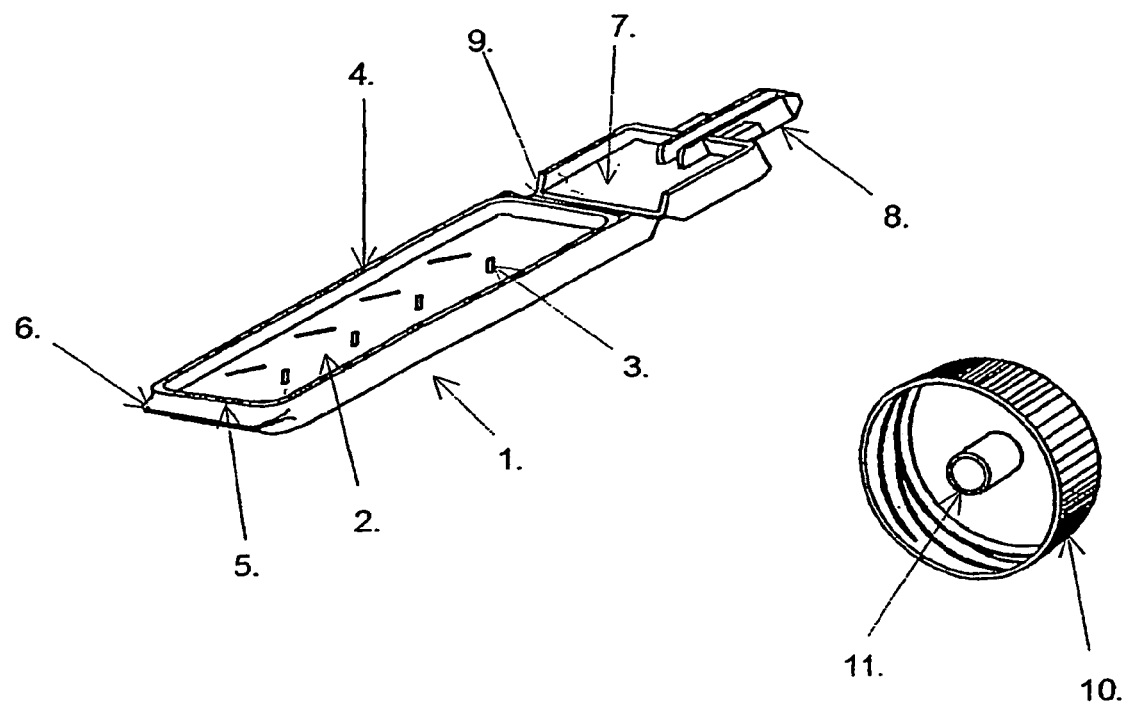
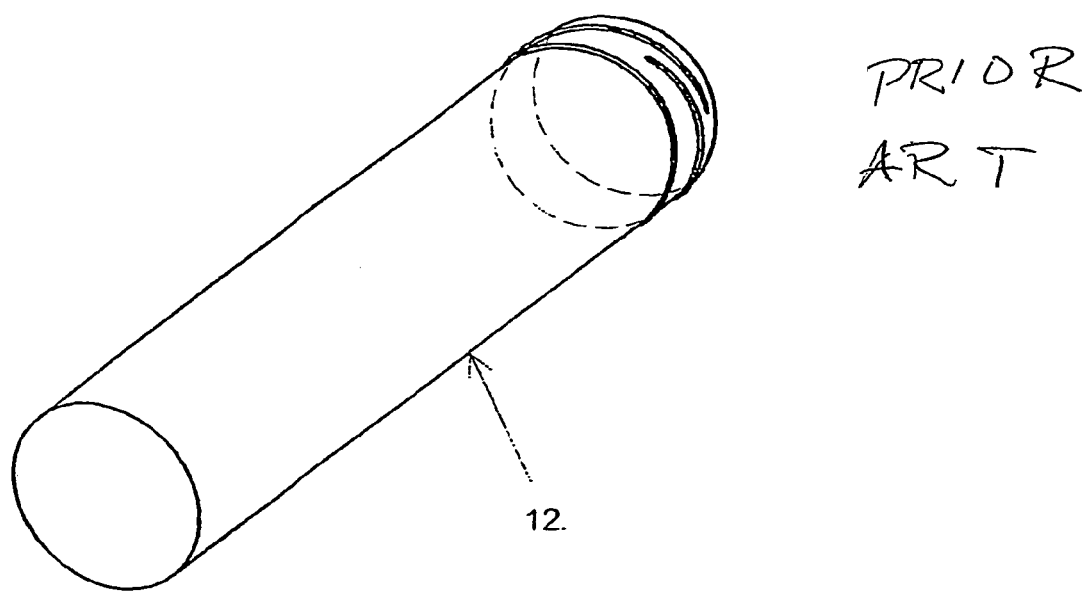
PRIOR ART
Fig. 1

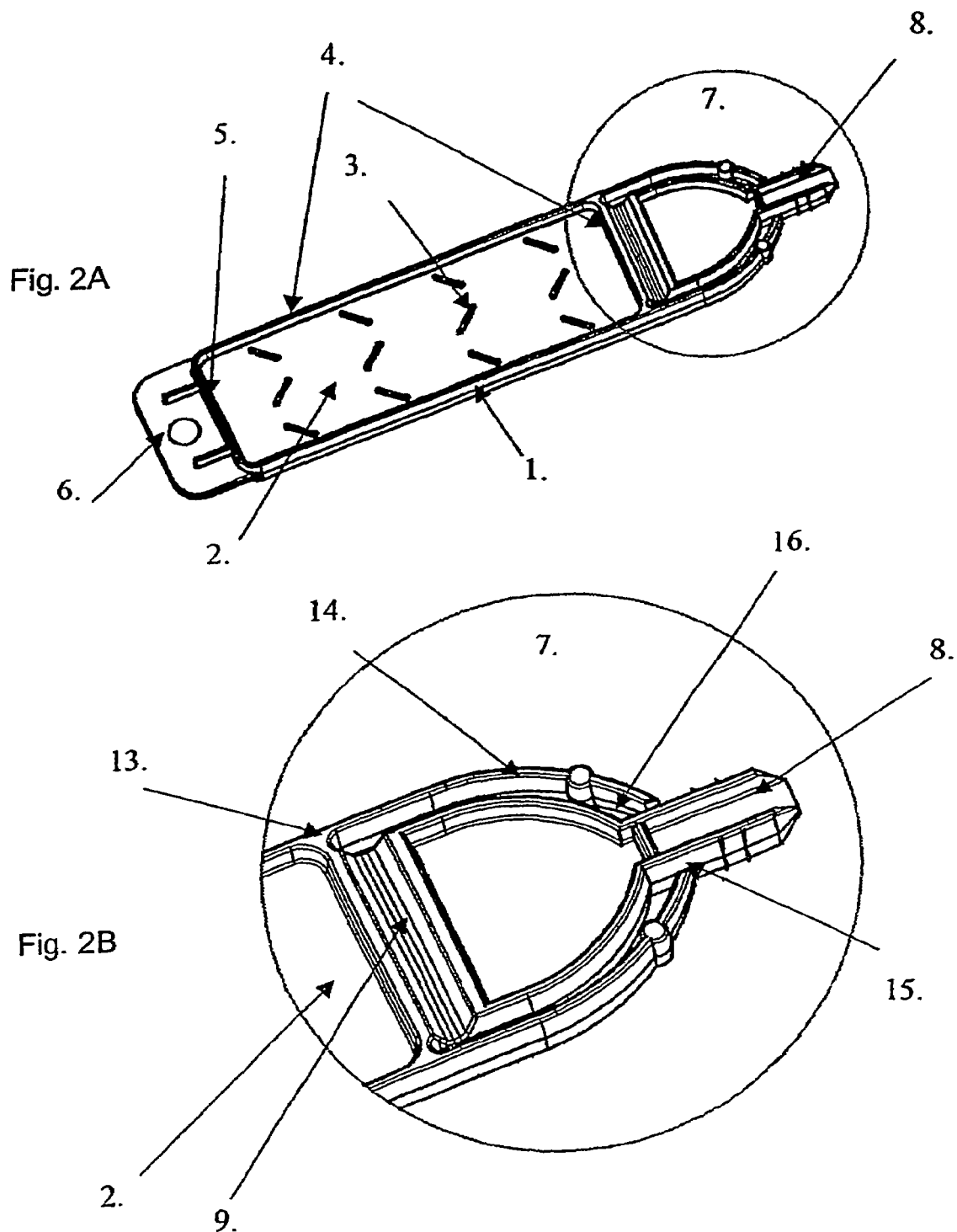

SUPPORT FOR GROWTH MEDIUM

The present invention relates to a hinged support for growth medium. This kind of support plate coated with a layer of a growth medium is intended for taking a microbial sample, transporting the sample and culturing/identifying microorganisms possibly occurring in the sample.

As a basic construction of a growth medium support plate in the art is known a sterile vial sealable with a cap whereto is connected a support plate member that carries the growth medium and is adapted insertable into the vial. This construction having no hinge at all is disclosed in FI Pat. No. 46,780. An equivalent embodiment is also described in FI Pat. Appl. 783,615.

When a solid surface must be tested, the handling of a growth medium support plate having no hinge or the like flexing point is difficult. It is practically impossible to place the support plate carrying the growth medium layer smoothly against the surface to be sampled chiefly because the cap connected to the support plate forms an obstacle and the support plate cannot be flexed. Furthermore, the pressure inflicted on the growth medium support plate during testing may vary from sample to sample depending on how high force applied to the surface being tested by the person performing the test. Moreover, if the cap is permanently connected to the growth medium support plate, the cap may cause a difficulty in the test by touching the surface being tested. Furthermore, contamination of the cap in such a contact with the tested surface is also possible thus forming a risk of transmitting infectious agents to the user and his environment. The risk of transmitted infection can be reduced by using a hinged growth medium support plate whose stem member can be flexed during testing by the cap in such a manner that the cap serving as a handle will not touch the surface being tested.

In fact, a great number of devices and methods intended for taking microbial samples from surfaces need a hinged structure of the connection between the growth medium support plate and its stem member.

In the art are known plural different embodiments of growth medium support plate structures with a hinged stem member. Examples of such designs are, among others, the Hygicult® dipslide devices manufactured by Orion Diagnostica, the HYcheck contact slide (by Difco Laboratories), the Envirocheck® contact slide (by Merck) and the Dip Slide device (by Oxoid).

In the embodiment described in patent publication GB 2,141,136, both ends of the growth medium support plate are provided with a hinged handle. The hinges are flexible thus easing the testing of a solid surface. The hinge is formed by V-shaped notches made symmetrically to the upper and lower side of the growth medium support plate made from a polymer material.

Patent publication WO 90/02169 discloses a device designed for sampling and incubation of anaerobic bacteria on a simple hinged support plate covered with a growth medium. The device design described in U.S. Pat. No. 4,865,988 features a similar kind of simply hinged growth medium support plate.

In the embodiment of EP patent publication 557,041, a flexible member connects the support plate to a handle (shaft). Thus, the growth medium support plate can be pushed out from the protective cover by the shaft and, respectively, pulled back into the protective cover after taking the sample. The handle is adapted to move in a narrow slot. This patent publication does not describe in greater detail the technical design of the flexible member serving as a hinge. The drawing of the disclosure only shows that the flexible member is substantially thinner than the actual support plate.

In mass production of hinged support plates, problems may occur in the connection of the cap to the support plate inasmuch as the support plate may travel on the assembly line in an unfavorable position. As a result, it can happen that the support plate during the assembly phase of the device in the manufacturing process may already be bent at the hinge into a disadvantageous position that retards or stops production or even causes a complete or partial failure of the assembly phase. When arriving on the assembly line into the position where the cap should mate with the hinged stem member of the support plate, such a bent hinge of the support plate misaligns the support plate stem member so much that the female coupler of the cap will not engage with the male coupler of the stem member. It is not uncommon to find the hinged stem member of the support plate thus bent in an incorrect position on the production line. The consequent loss of production volume and time may invoke substantial economic and material expenditures. This problem appears in a particularly accentuated form in conjunction with support plates having the hinge situated in the upper end of the support plate stem member.

Another common problem hampering the use of growth medium support plates of conventional design appears during sampling so that the lower end of the support plate tends to rise upward when the pressing force imposed by the testing person happens to be inflicted at the hinge. Then, the sampling pressure may be different by an order of magnitude at the opposite ends of the growth medium support plate thus causing inaccurate testing.

The above-described problems hampering the manufacture of a growth medium support plate and use thereof can be eliminated by virtue of a growth medium support plate according to the present invention whose essential characteristics will be evident from the appended claims. Particularly the structure of the hinged portion of the support plate is different from conventional designs.

The growth medium support plate according to the invention comprises a body part consisting of a slide portion covered by a growth medium and a hinged portion comprising fixed projections of the body part and a stem portion connected to the projections. To the stem portion is connected by conventional techniques a cap designed to seal the support plate after sampling in an appropriate storage and transport vessel.

Next, the invention will be described in greater detail by making reference to annexed drawings in which FIG. 1 shows the basic elements (support plate and hinged portion) of a conventional growth medium support plate (Hygicult®) with its vial and cap;

FIG. 2A shows the basic elements of a growth medium support plate according to the invention;

FIG. 2B shows in detail the hinged portion of the support plate according to the invention with the technical design thereof;

Figures 3A, 3B:
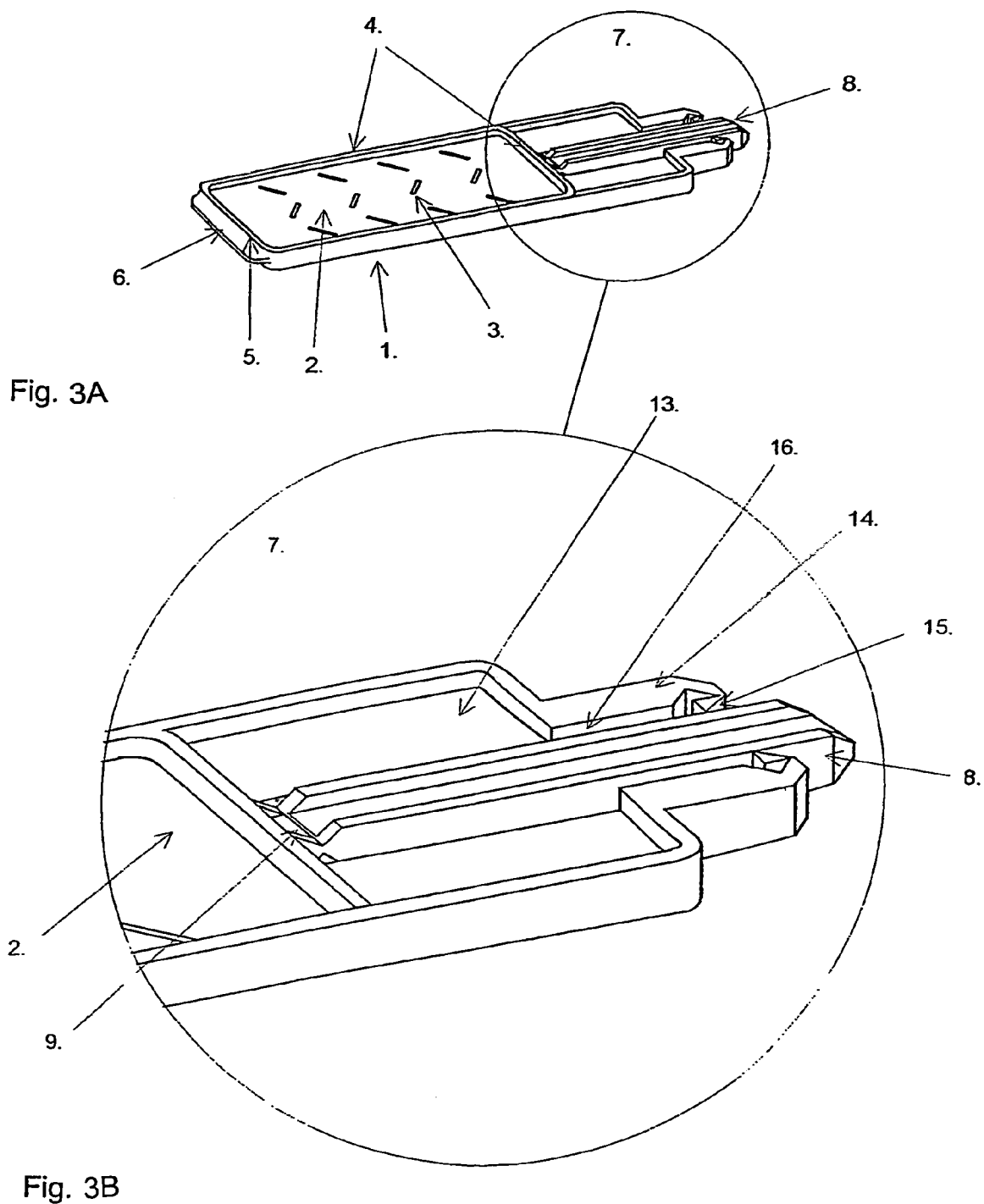
FIG. 3A shows the basic elements of an alternative embodiment of a growth medium support plate according to the invention.
FIG. 3B shows in more detail the alternative technical design of the hinged portion of the growth medium support plate according to the invention.

Next, the details of conventional constructions and those implemented according to the invention will be discussed more precisely.

State-of-the-art hinged support plates covered with a growth medium have an almost identical construction (FIG. 1). Varying within certain limits, the size of the plates typically is about 20 mm by 70 mm. The support plate 1 itself comprises a narrow growth medium slide portion 2 having a smooth surface or contoured with bumps or dimples 3. The bumps or dimples forming different patterns, such as lines or a grid or ridges in V-shape, help the growth medium adhere to the surface of the plate and stay fixed thereto. The growth medium support plate may be either one-sided or two-sided. In a two-sided plate, both sides may carry the growth medium. The growth medium can be optimized for a single microorganism or developed to selectively support plural different microorganisms.

Furthermore, the structure of the support plate can be designed such that allows different growth media to be placed selectively on a single side of the plate. By virtue of varying the height of the border walls 4 on the growth medium support plate, a suitable amount of growth medium for a given testing purpose can be placed on the growth slide of the support plate. One end (lower end) 5 of the growth medium support plate may be blunt or include a short extension 6. The other end (upper end) of the support plate includes a hinged portion 7. The hinged portion is comprised of a stem member 8 and a hinge 9. In the embodiment shown in FIG. 1, the hinge extends from edge to edge across the support plate. Stem member 8 joins cap 10 with the support plate by means of a female coupler 11 made on the inner side of the cap. Holding by fingers from the cap, the support plate may be inserted into a transparent, tubular vial 12. The cap may be either a threaded cap or a snap-on closure. The vial can also have a flattened cross section, whereby a snap-on closure must be used. The cap may also be produced to be an integral portion of the support plate. Respectively, alternative cross-sectional shapes of the transparent vial may be contemplated, such as a vial having a square or rectangular shape. Obviously, the design of the vial may be varied widely.

In FIG. 2 is shown a growth medium support plate 1 based on a hinge construction according to the invention. As is evident from FIG. 2A, the basic construction of the support plate does not differ substantially from the conventional design of a support plate illustrated in FIG. 1. The hinged portion 7 of the support plate according to the invention is shown in enlarged scale in FIG. 2B. In this construction, the stem member 8 of the hinged portion is freed from its both lateral sides by gaps 16 into a separate member whose connection to the slide portion 2 of the growth medium support plate is designed to serve as a hinge 9. Cap 10 is connected to the support plate stem member 8 by means of female coupler 1 of the cap. Thus, the gaps 16 provided in the support plate body part 13, more specifically between the body part projections 14 and the support plate stem member 8, allow the flexing of the hinged stem member 8 at hinge 9 under a bending force. During initial production steps, the hinged portion, particularly the stem portion 8 thereof, is kept immobilized in accordance with the invention with the help of a fixing member 15 located on both sides of the stem member. The function of the dual fixing member 15 is to connect the distal end of the projection 14 of the support plate body part 13 to the respective distal end of the support plate stem member 8 so that the stem member is stiff flexibly connected to the support plate body part.

In FIG. 3 is shown a growth medium support plate 1 based on an alternative embodiment of the hinged portion 7 of the support plate in accordance with the invention. As is evident from FIG. 3A, the basic construction of the support plate does not differ substantially from the conventional design of a support plate illustrated in FIG. 1. The reference numerals of the diagram discussed below are equivalent to those of FIG. 2A. The hinged portion of the support plate according to the invention is shown in enlarged scale in FIG. 3B. The stem member 8 extending from the hinged portion is freed from its both lateral sides by gaps 16 into a separate member whose connection to the slide portion 2 of the growth medium support plate is designed to serve as a hinge 9. A cap 10 is connected to the support plate stem member 8 by means of a female coupler 11 of the cap. Thus, the gaps 16 provided in the support plate body part 13, more specifically between the body part projections 14 and the support plate stem member 8, allow the flexing of the hinged stem member 8 at hinge 9 under a bending force. During initial production steps, the hinged portion, particularly the stem portion 8 thereof, is kept immobilized in accordance with the invention with the help of a fixing member 15 located on both sides of the stem member. The function of the dual fixing member 15 is to connect the distal end of the projection 14 of the support plate body part 13 to the respective distal end of the support plate stem member 8.

Figure 4:
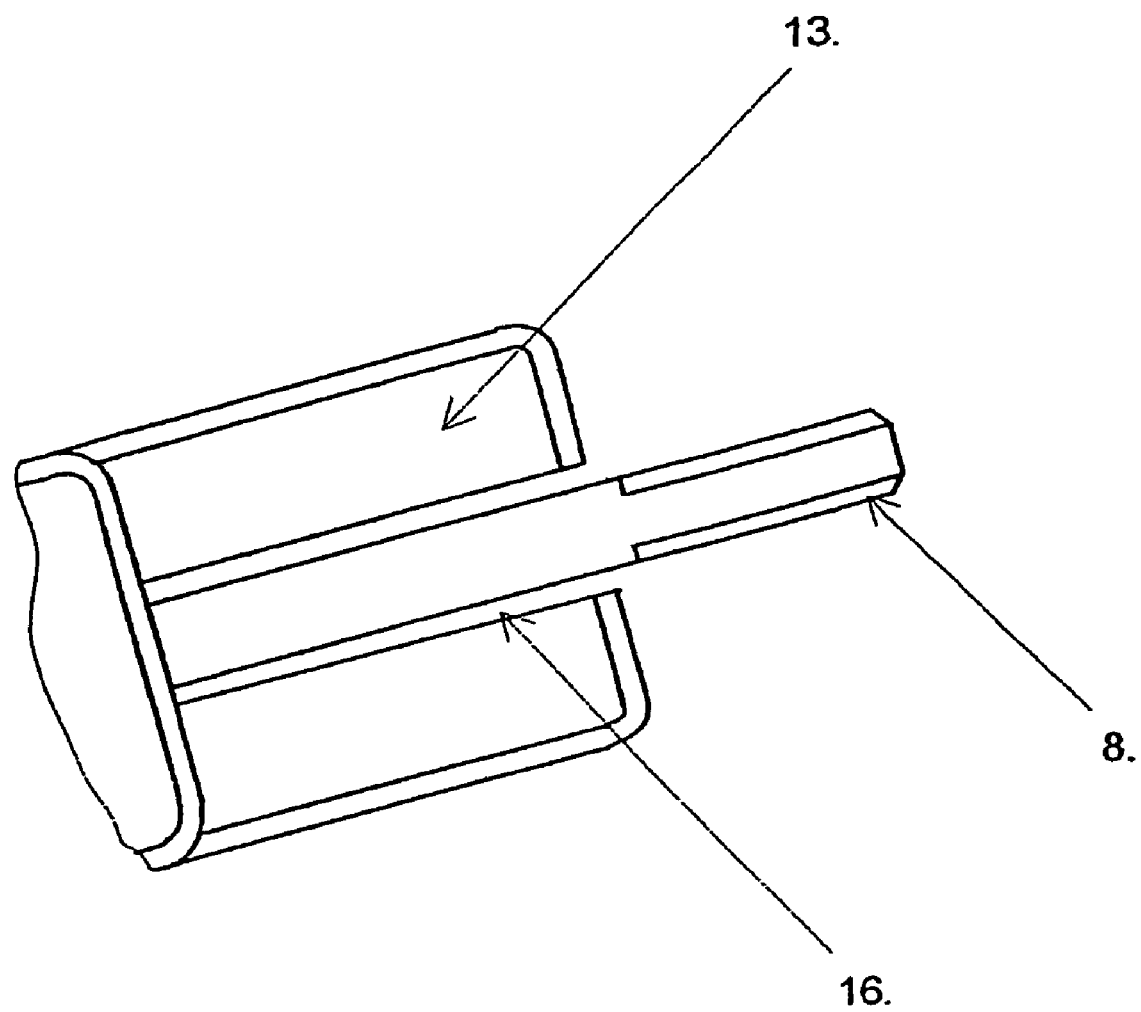
FIG. 4 shows an exemplary embodiment of the leaf-spring-like hinge construction according to the invention.

One further alternative structural embodiment according to the invention may be such as shown in FIG. 4. This construction is based on designing the support plate stem member 8 to act as a leaf spring permitting lateral flexing and being separated from the support plate body part 13 by gaps 16. A leaf-spring implementation does not necessarily need the fixing member 15 inasmuch as this construction can inherently keep the stem member immobilized and thus properly aligned in a secure position during the production steps.

By virtue of a properly designed stiffness of the leaf-spring portion, the flexural spring can be made such that it stays immobilized during production even without locking but nevertheless can flex under a bending force. While this embodiment is otherwise similar to that described above, it lacks the hinge grooves at its hinged portion, but instead has the support plate stem member made thinner at its base portion. A support plate stem member thus designed inherently tends to assume its rest position.

The construction according to the invention offers a further benefit of giving a better feel and touch to the sampled surface during testing. Depending on the specific design of the support plate body part, a properly shaped body part 13 (FIG. 4), the body part 13 with its projections 14 (FIG. 3B) or, alternatively, the projections of the body part (FIG. 2B) provide hereby convenient support to the user of the contact slide and facilitate the application of a uniform contact pressure over the entire area of the sampled surface.

The leaf-spring construction of the support plate is capable of automatically adjusting the sampling pressure applied to the surface being tested. During testing, the pressure applied to the tested surface is determined not only by the stiffness, thickness, width and other parameters of the leaf-spring structure, but also by the material and dimensions selected for this portion and, naturally, by the force applied by the user via the cap on the leaf-spring member.

The distal end of the projection extending from the support plate body part can be affixed the stem member by different kinds of break-off joints accomplished by such techniques as casting, welding, glueing or melting. Alternatively, the distal end of the support plate body part projection or the edge of the stem member can be shaped such that the mating surfaces of these member portions make a frictional contact with each other. To this end, the distal portion of the support plate projection can be made, e.g., curved or provided with a bump that coincides with a notch on the stem member. Conversely, the distal end of the stem member can be made to comply with the contour of the projection extending from the support plate body part.

In the present culture incubation and transportation slide embodiment, the support plate acting as the growth medium carrier is connected by a stem member to the vial cap by means of a coupler forming an integral part of the cap. The hinged portion of the support plate can flex in the intended fashion only after the distal end of stem member is pushed into the coupler of the cap. The stem member is released from its immobilized state according to the invention only after the edges of the cap coupler during assembly break off the connection (fixing member) between the distal end of the stem member and the projection extending distally from the support plate body part. After the stem member is thus freed, it becomes readily flexible at its hinged portion. Then, the stem member can be flexed relative to the horizontal support plane in two opposite directions, that is, upward and downward. During sampling, the stem member only needs to be flexed upward. In this operation, the projections of the support plane body part do not interfere with the flexing of the stem member. Herein, the freed stem member acts as a spring (shock absorber) when the culture slide, or the support plate, covered with the growth medium is pressed against the surface to be tested. With a proper design of the support plate body part, it becomes possible to utilize the body part projections for re-aligning the support plate after sampling. To this end, the body part projections can be made curved, e.g., at the points they touch the stem member. When so desired, the distal end of the body part projection can be compliant with the contour of the stem member so that, after the fixing member is broken away, the tip contour of the body part projection mates with shape of the stem member and thus always relocates the support plate accurately in its advantageous initial position if such a function is desired by the user.

The growth medium support plate according to the invention equipped with a cap can be readily inserted into a vial (cover) protecting the support plate. The vial is intended for transportation of microbiological samples from the testing site to a laboratory. Thus, the support plate covered with a growth medium functions both as a sampling slide and a growth medium platform for the incubation of microorganisms. The vial also serves to protect the sample from external contamination during both the transportation and culturing (incubation) of the sample to identify the microorganisms possibly collected thereto. Conversely, the vial prevents infectious microbes from escaping to the environment. One further task of the vial is to maintain a steady level of humidity about the growth medium support plate.

The support plate may also be relocated by virtue of proper shaping of the exterior side of the female coupler made on the interior side of the cap. Resultingly, the support place resumes after testing its initial unbent position as a result of the cooperation of the support plate body part projections and the appropriately shaped exterior side of the female coupler. This may take place so that, e.g., at the relocation of the support plate stem member into the gap between the opposed projections of the support plate body part, the stem member assumes a immobilized position when the projections lock, e.g., on small notches made on the exterior side of the female coupler. Herein, the length and contour of the support plate body part projections must be made compatible with the notches on the coupler. Having the support plate thus relocated into its immobilized position, it cannot touch the interior wall of the vial when the support plate is being inserted into or stored in the vial.

The immobilization locking arrangement according to the invention of the stem member can be implemented independently from the construction of the hinged portion of the stem member. The hinge may be formed by making on both sides of the support plate hinged portion a V-shaped, U-shaped or semicircularly shaped notch or the like thinned portion or by thinning the stem member in some other manner at the desired location of the hinge.

Independently from the technical implementation of the hinged portion (with a discrete hinge or using some other design), its properties can be modified by varying the width, thickness and shape (triangular, rectangular, etc.) of the hinged portion.

Obviously, the dimensions of the hinged portion must be selected to meet the needs of a specific application. If the dimensions of the hinged portion are changed substantially, also the function of the support plate and its proportions will be affected.

In the support plate construction according to the invention the hinged portion of the stem member and the lateral projections of the support plate body part are separated from each other by gaps on both sides, whereby a stem member is formed as an extension of the support plate. According to a preferred embodiment of the invention, the structure of the stem member projecting from the hinged portion is such that the lower end of the stem member connected to the slide portion of the growth medium support plate via the hinged portion is almost as wide as the support plate while the upper end of the stem member is made tapering, that is, the stem member looks "triangular" as being distally tapered in its lateral width. To implement this shape, the two sides of the stem member may be made curved as shown in FIG. 2 or the sides can be straight. The lower end of the stem member need not necessarily be as wide as shown in the diagram, but may also be made narrower. The projections of support plate body part serve as fingerholds of the support plate, whereby they provide the user extra grip during testing and improved feel when the support plate is being contacted with the surface being tested. As is evident to a person skilled in the art, the stem member extending upward from the hinged portion need not necessarily have a triangular shape, but instead may also be made rectangular, that is, having a constant width over the entire length of the stem member as shown in FIG. 3.

When so desired, the projections extending from the hinged portion and the body part of the support plate, or equivalent members, may be injection molded at both ends of the support plate.

Generally, the support plate is made from a polymer. Suitable plastic materials are, e.g., polyethylene, polypropylene and polystyrene, among the like thermoplastic polymers the most preferred one being polypropylene.

Obviously, a person skilled in the art can combine different plastic materials, composites thereof and other materials so as to obtain enhanced properties such as improved stiffness, durability, elasticity or resistance under flexing, only to name a few.

The hinge constructions according to the invention can be utilized in a test kit that includes a culture slide formed by a support plate covered by a growth medium for sampling different kinds of surfaces. As mentioned above, the support plate is also suited for testing liquids. Furthermore, the support plate of the present growth slide may be used for transportation and incubation of microorganisms possibly captured in the sample.

What is claimed is:

1. A growth medium support plate comprising:
   an essential planar body part extending therefrom;

a stem member for connecting a cap to said support plate, the stem member being connected to said body part so as to have a position co-planar with the body part and a position inclined to the plane of the body part, wherein said support plate includes at least one fixed projection extending from and co-planar with said body part adjacently to the stem member and the stem member having in said position coplanar with the body part a releasable connection to said at least one fixed projection.

2. The growth medium support plate of claim 1, wherein said at least one projection of said support plate body part is configured to make contact with said stem member by means of fixing members.

3. The growth medium support plate of claim 2, wherein said fixing members are configured to make contact with said stem member by a break-off connection.

4. The growth medium support plate of claim 3, wherein said break-off connection is implemented by means of injection molding, welding, gluing or melting.

5. The growth medium support plate of claim 3, wherein said break-off connection is configured to undergo its breaking-off action in conjunction with the assembly of said cap on said stem member.

6. The growth medium support plate of claim 1, wherein said stem member is configured to make a frictional contact with said at least one projection of said support plate body part.

7. The growth medium support plate of claim 2, wherein the body part is furnished with projections extending on both sides of said stem member.

8. The growth medium support plate of claim 1, wherein said stem member has a distally tapering shape in the plane of its lateral width.

9. The growth medium support plate of claim 1, wherein said body part or the at least one projections thereof are shaped to serve as fingerholds.

10. The growth medium support plate of claim 1, wherein said stem member is implemented as a leaf spring.

11. The growth medium support plate of claim 1, wherein the material of said support plate is polyethylene, polypropylene or polystyrene, advantageously polypropylene.

12. Test kit for taking a sample from surfaces or, alternatively, liquids, transporting the sample and identifying/incubating microorganisms possibly occurring in the sample, wherein said test kit includes the growth medium support plate of claim 1.

* * * * *